United States Patent
Jaralla

(10) Patent No.: US 7,320,245 B2
(45) Date of Patent: Jan. 22, 2008

(54) CORROSION TESTING APPARATUS

(75) Inventor: Abdulghani Jaralla, Auckland (NZ)

(73) Assignee: Saudi Arabian Oil Company, Dhahran (SA)

( * ) Notice: Subject to any disclaimer, the term of this patent is extended or adjusted under 35 U.S.C. 154(b) by 145 days.

(21) Appl. No.: 10/533,490

(22) PCT Filed: Nov. 18, 2003

(86) PCT No.: PCT/US03/37251

§ 371 (c)(1),
(2), (4) Date: Nov. 30, 2005

(87) PCT Pub. No.: WO2004/046692

PCT Pub. Date: Jun. 3, 2004

(65) Prior Publication Data

US 2006/0162432 A1    Jul. 27, 2006

(51) Int. Cl.
*G01N 17/04* (2006.01)
(52) U.S. Cl. ............................ 73/86; 73/431; 73/866.5; 204/404; 324/71.2
(58) Field of Classification Search .............. 73/866.5, 73/431, 86; 204/404; 324/71.2
See application file for complete search history.

(56) References Cited

U.S. PATENT DOCUMENTS

| | | | | |
|---|---|---|---|---|
| 2,464,233 A | * | 3/1949 | Hughes et al. | 73/53.05 |
| 2,519,323 A | * | 8/1950 | Shank et al. | 73/86 |
| 3,014,789 A | * | 12/1961 | Wolber | 422/53 |
| 3,627,493 A | * | 12/1971 | Manley | 422/53 |
| 3,632,495 A | * | 1/1972 | Watson | 204/404 |
| 4,097,341 A | * | 6/1978 | Schell et al. | 205/775.5 |
| 4,179,920 A | * | 12/1979 | Schuller et al. | 73/86 |
| 4,422,917 A | | 12/1983 | Hayfield | |
| 4,468,613 A | * | 8/1984 | Slough et al. | 324/71.2 |
| 4,585,579 A | | 4/1986 | Bommaraju et al. | |
| 4,623,440 A | | 11/1986 | Cairns | |

(Continued)

FOREIGN PATENT DOCUMENTS

JP    61065137    4/1986

(Continued)

OTHER PUBLICATIONS

International Search Report for International Patent Application PCT/US03/37251.

*Primary Examiner*—Hezron Williams
*Assistant Examiner*—David A. Rogers
(74) *Attorney, Agent, or Firm*—Abelman, Frayne & Schwab

(57) ABSTRACT

A rotational test electrode assembly for use in a corrosive fluid environment as shown in FIG. 1 that includes a generally cylindrical heat and electrically conductive member (110) having an annular portion (112) and a solid portion (114): a heating device (130) positioned inside of the annular portion and in heat exchanging relation with the solid portion of the conductive member; a corrosion resistant external protective member (140) that surrounds a portion of the heat conductive member in close-fitting relationship; mounting means for attaching a rotational electrode (150) in close fitting heat and electrically conductive relation, the electrode being selected from the group consisting of cylindrical and disk electrodes; and an electrical connector for receiving a plurality of external electrical connectors that is mounted on the protective member opposite the portion of the conductive member on which the rotational electrode is mounted.

18 Claims, 4 Drawing Sheets

U.S. PATENT DOCUMENTS

| | | | |
|---|---|---|---|
| 4,627,905 A | * | 12/1986 | Garner et al. .......... 204/196.06 |
| 4,889,608 A | | 12/1989 | Eickmann |
| 5,006,786 A | | 4/1991 | McKubre et al. |
| 5,579,354 A | | 11/1996 | Sakai |
| 6,621,263 B2 | | 9/2003 | Al-Janabi et al. |
| 2005/0223829 A1 | * | 10/2005 | Mayeaux ................... 73/866.5 |

FOREIGN PATENT DOCUMENTS

JP  01155264 A  *  6/1989

* cited by examiner

CORROSION TESTING APPARATUS

FIELD OF THE INVENTION

This invention relates to apparatus useful in investigating corrosion phenomenon that effect industrial equipment and, more particularly, to apparatus that is utilized in determining the electrochemical behavior of metals and the performance of corrosion inhibitors under controlled conditions.

BACKGROUND OF THE INVENTION

A wide variety of apparatus and methods have been developed by corrosion and design engineers for evaluating the effect of corrosion-producing fluids passing in contact with industrial equipment, such as heat exchangers, reactors, pipelines, and the like. Apparatus and methods for in situ testing of effects on pipelines are known, as are numerous laboratory techniques. Laboratory bench scale test devices known to the prior art include rotating disk and rotating cylinder specimens that are immersed in corrosive fluid media to determine the effects on, e.g., the types of metals that come into contact with comparable fluids under industrial conditions. The rotational movement of the specimens can be varied to simulate actual hydrodynamic conditions.

Many production processes and material transport systems in industrial plants involve heat transfer across a metal-fluid interface and mass transfer to or from that interface, including the buildup of scale deposits and loss of material due to corrosion. Materials selected for industrial applications must, therefore, be able to withstand or at least resist adverse effects that are initiated or accelerated by heat and mass transfer. In order to make the optimum choices, corrosion and design engineers need an understanding based on data relating to the effects of heat and mass transfer on material degradation from corrosion. Little investigative work on corrosion and corrosion prevention under heat and mass transfer conditions has apparently been reported in the literature.

It is therefore an object of the present invention to provide corrosion testing apparatus to examine the electrochemical behavior of metals and the performance of organic and inorganic inhibitors or passivators under conditions of controlled and quantified heat and mass transfer.

Another object of the invention is to provide a means for obtaining data to quantify the effect of various conditions and factors by simulating industrial conditions effecting the corrosion behavior of metals and the performance of chemical additive corrosion inhibitors.

A further object of the invention is to provide an apparatus that permits the bench scale investigation of industrial corrosion factors with minimum costs and that permits the testing and evaluation of inhibitors without risk of direct or indirect damage to the industrial facilities.

SUMMARY OF THE INVENTION

The above objects and other advantages are achieved by providing a single rotating electrode apparatus that is configured to receive either of a pair of rotating electrodes in heat conductive mounting relation in order to obtain quantified data under heat transfer conditions. The first of the pair of electrodes is a rotating disk electrode (RDE) and the second is a rotating cylinder electrode (RCE). Both the RDE and RCE are interchangeably mountable for rotation on the same rotational electrode supporting shaft in a test stand to provide economy of materials and measuring devices.

In a particularly preferred embodiment, the interchangeable rotating electrode supporting shaft is provided with an internally mounted heating element in the form of an electrical resistance heating device. The heat conductive member can be fabricated from brass in the form of a hollow cylinder proportioned to receive the heating device and its associated electrical leads. The heating device is positioned proximate to a metal heat conductive supporting member that efficiently conducts the heat generated to an external surface that is in contact with either a disk electrode or a cylindrical electrode specimen.

In a particularly preferred embodiment, a plurality of thermocouples or thermistors are embedded in the conductive member to provide temperature readings at positions closely adjacent to the point of attachment of the rotating electrode, as well as proximate and displaced from the heating device. The leads from the thermocouples also extend axially to the upper end of the rotating electrode shaft to a plug, socket or other terminal connection. The thermocouples are connected to a remote temperature display and recording device to provide the necessary data for controlling the power to the heating device to meet the desired temperature of the specimen electrode.

An electrically conductive lead is also attached to the metal conductive member on which the electrodes are mounted in heat and electrical conductive relation. This lead also extends to the plug or socket termination for subsequent connection to a power source.

In order to meet the electrical power requirements of the rotating electrode assembly during operation, the drive shaft that rotates the assembly is provided with a slip-ring assembly having a plurality of electrical conductors corresponding to the conductors required to provide current to the electrode support, heating device, and for each of the plurality of thermocouples mounted in the conductive member. Each of the leads from the slip-rings is terminated in a plug or socket for mating engagement for its counterpart in the end of the rotating electrode shaft. As an alternative, the plurality of leads from the slip-rings and the rotating electrode can be individually joined by appropriate insulated connectors.

A corresponding brush set is provided with appropriate leads to provide the necessary electrical power input to the slip-rings during rotation of the driveshaft. It will also be understood that the leads from the respective brushes are operably connected to one or more units for display and, optionally, recording of the temperature of each of the plurality of thermocouples; a separate power control and display unit is connected to the leads of the heating device. A separate power control unit and display is also provided for the working electrode. A single ground connection is utilized in a preferred embodiment in order to minimize the number of wires required.

In order to protect and isolate the heat conductive member from the corrosive fluid in which the unit is immersed, it is provided with a fluid-tight protective cover or housing. The protective cover material is also to be electrically non-conductive in order to isolate the rotating electrodes from stray currents.

The protective layer can be selected from such highly corrosion resistant and electrically insulative polymeric materials as polytetrafluoroethylene (PTFE). The protective housing is preferably provided in the form of a hollow cylindrical member with a wall thickness that provides a rigid construction. The cylindrical metal conductive member can then be positioned inside of the close-fitting hollow polymeric cylinder.

In order to provide a rigid point of attachment for the driveshaft coupling, the hollow protective housing is preferably extended well above the end of the internal conductive member to form a portion that also extends well beyond the top of the polarization cell when the rotating electrode is in an operational position. In order to provide additional rigidity to the upper end of the protective housing member at the point of attachment to the driveshaft coupling, a close-fitting cylindrical metal sleeve member having a flanged top is inserted into the hollow end of the protective member. This internal sleeve is designed to provide sufficient strength and rigidity to permit set screws or other attachment means to rigidly secure the driveshaft to the rotating electrode shaft. In order to maintain electrical isolation of the electrode, the reinforcing sleeve should not come into contact with the heat conductive member.

The lower portion of the metal conductive member is threaded externally in order to receive a cooperatively threaded rotating cylindrical electrode element that serves as the test specimen. In the preferred embodiment, the rotating cylinder electrode is threaded onto the conductive member to a position that substantially surrounds the internal heating device to minimize the distance heat must be transmitted through the conductive member to elevate the temperature of the rotating cylinder electrode specimen to the desired degree. In this regard, thermocouples or thermistors are positioned in the conductive member adjacent the mid-point of the rotating cylinder electrode when it is in position for operation.

In order to protect the lower portion of the cylindrical heat conducting member, an internally threaded polymeric protective cap in the form of a cup is positioned to provide a fluid-tight seal to the base of the rotating cylinder specimen when assembled to the conductive member. It will also be understood that the upper portion of the protective member forms a fluid-tight seal with the upper rim of the rotating cylinder when it is threaded onto the conductive member. Internally threaded caps of different depths can be provided to accommodate rotating cylinder specimens of different axial lengths. The direction of the respective threads is opposite that of the direction of rotation to insure that the electrode will not become loosened during operation.

In order to securely mount the rotating disk electrode, an internally threaded opening is provided in a smooth flat surface at the lower end of the supporting shaft to receive a cooperatively threaded attachment shaft projecting from the upper surface of the RDE. When the RDE is tightly threaded onto the end of the heat conductive member, the mating surfaces provide an efficient heat conducting interface boundary.

In a particularly preferred embodiment, a recessed or setback shoulder is provided at the upper end of the RDE in order to provide a mating surface for engagement with the projecting end of the hollow cylindrical protective member. This mating engagement is also intended to provide a fluid-tight seal that will prevent corrosive fluid incursions and contact with the metal conductive member.

The data obtained from the apparatus is applied utilizing known algorithms and methodologies known to those of ordinary skill in the art to calculate the surface temperature of a rotating cylinder electrode and/or disk that is transferring heat to the fluid in the test cell. Further calculations are undertaken to determine the effects of laminar flow conditions and turbulent flow conditions on the vulnerability of the test cylinders and disks to the corrosive fluid(s) in the test apparatus. Similarly, the data obtained is used to determine the effects of corrosion inhibitors and metal passivation additives under various temperature and simulated flow conditions.

The apparatus and method of the invention provide for the heating of either the RDE or the RCE, or both simultaneously, to a temperature that exceeds the temperature of the surrounding fluid in the test solution chamber. The invention thereby allows simulation of conditions of heat transfer such as those that exist in heat exchangers of the tube type where the temperature at the inlet end can vary considerably from that at the discharge end. Furthermore, the temperature differentials between the heat exchanger tubes and the surrounding fluid also changes between the inlet and outlet ends. Prior art tests and/or calculations that are based upon only a single temperature will only reflect the conditions existing at a particular portion of a pipe or tube in the heat exchanger. Utilizing the apparatus and method of the present invention, the temperature of the rotating cylinder electrode can be varied by adjusting the heat generated by the heating device over a range of temperature differentials, thereby more accurately replicating actual industrial conditions.

BRIEF DESCRIPTION OF THE DRAWINGS

The invention will be further described below and with reference to the attached drawing sheets in which.

DETAILED DESCRIPTION OF THE INVENTION

Figures 1, 1A:
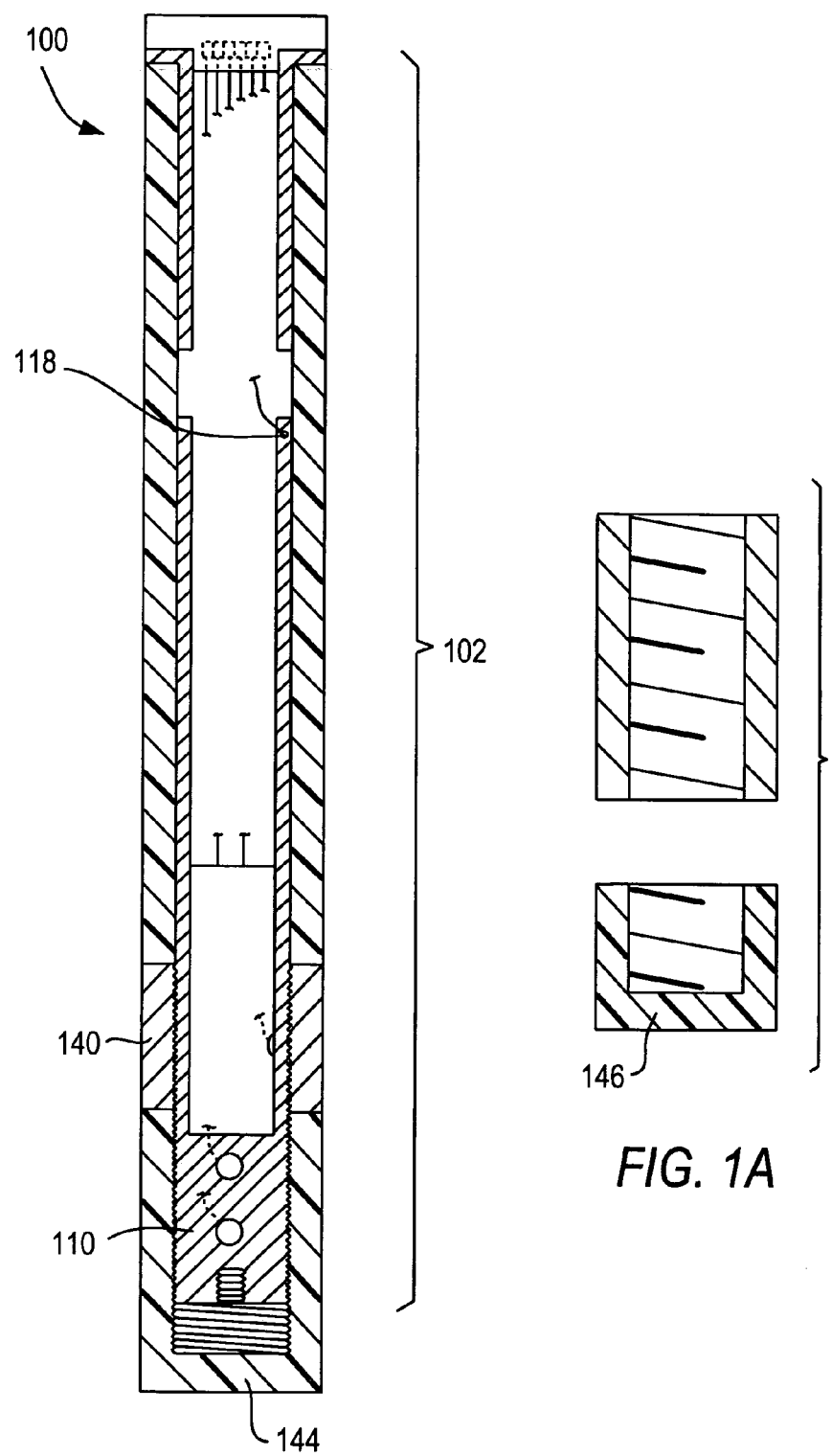
FIG. 1 is a schematic elevational view, partly in cross-section, of an embodiment of the invention used with a cylindrical electrode.
FIG. 1A is a further preferred embodiment similar to FIG. 1 illustrating an axially elongated cylindrical electrode for use in the invention.

Referring now to FIG. 1, there is illustrated the rotating test electrode assembly of the invention that is arranged for use with a cylindrical electrode specimen. Conductive member 110 consists of upwardly extending annular member 112 defining an opening 116 and terminating in an integral solid base portion 114. The lower portion of the conductive member 110 is provided with external threads that cooperatively engage mating internal threads on cylindrical electrode specimen 150. A protective member 140 extends from the upper mating surface of electrode 150 to a terminus above the end of annular portion 112.

A heating element 130 is securely positioned in annulas 116. Electrical leads extend from the heating device 130 to a electrical terminal in the form of socket 138 positioned in the upper end of assembly 100.

In a preferred embodiment, a plurality of thermocouples 113 are positioned in the conductive member 110 proximate the heating device 130 and the lower end of solid portion 114 proximate the point of attached of the disk electrode, as described below in connection with FIG. 2.

With continuing reference to FIG. 1, a second portion of the protective member 140 takes the form of an interiorally threaded polymer cup 144 which is received on the lower end of conductive member 110 to make a fluid-tight contact with the bottom edge of electrode 150.

With further reference to FIG. 1, a reinforcing flanged metal sleeve 160 is secured in the upper open end of protective member 140 to provide a rigid point of attachment for a coupling member, as will be described further below. Electrical leads extending from socket 138 are connected to the working electrode at a point 118 in the side wall of annular portion 112, and to the thermocouple leads.

It is also to be noted that an air gap 148 has provided between the reinforcing sleeve 160 and the hollow cylindrical portion 112 in order to electrically isolate the working electrode 150 from any stray currents that might be produced by the motor or other electrical controls used to power the apparatus.

As will be seen from FIG. 1A, the axial dimension of the cylindrical electrode can be extended as in 150A, while the protective cup portion 144A will be reduced in height. This feature of the invention provides added flexibility to the testing of cylindrical electrodes, while still maintaining the ability to utilize the rotational test electrode mounting shaft with a disk electrode, as will be described below.

Figure 2:
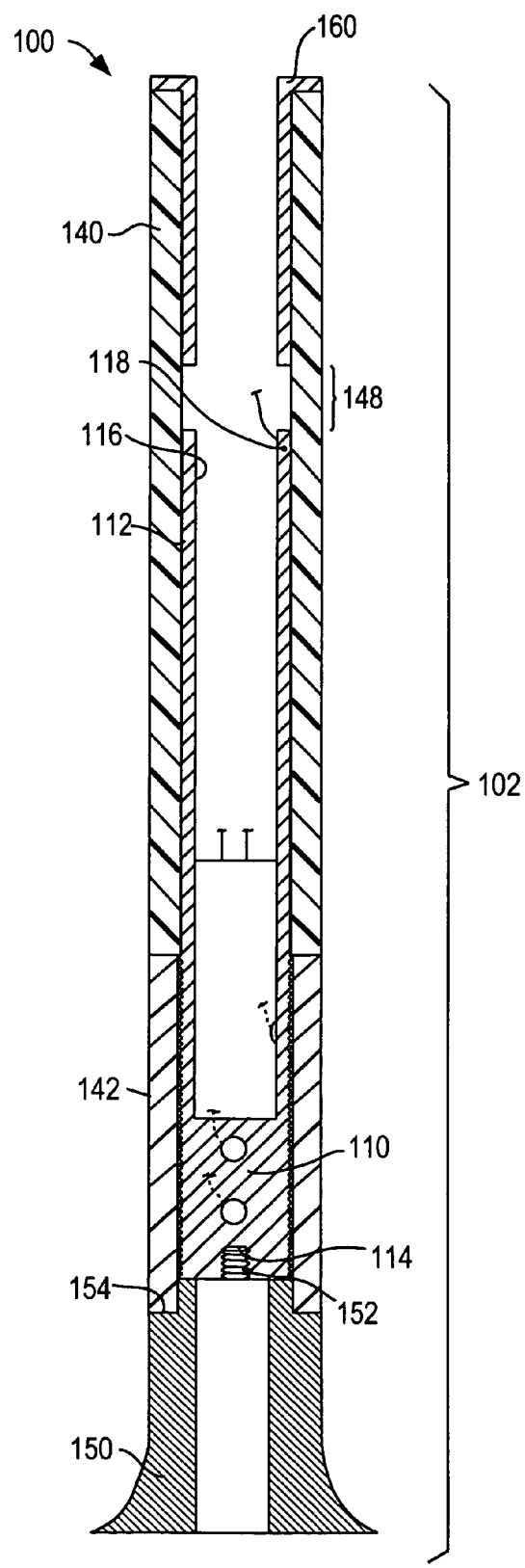
FIG. 2 is a schematic illustration of the invention similar to FIG. 1 for use with a disk electrode.

Referring now to FIG. 2, it will be seen that the same principal structural elements are utilized for mounting disk electrode 156 on the lower end of conductive member 110. The threaded orifice 114 receives correspondingly threaded shaft 152 extending from the upper surface of disk electrode 156. A second portion of the protective member in the form of sleeve 142 is mounted on the lower portion of conductive member 110 and engages the shoulder 154 when the unit is assembled for operation. In this embodiment, it will be understood that the cylindrical electrode 150 has been removed and in its position has been placed protective sleeve 142 which forms a fluid-tight seal with the lower portion of the protective member 140.

Figures 3, 3A:
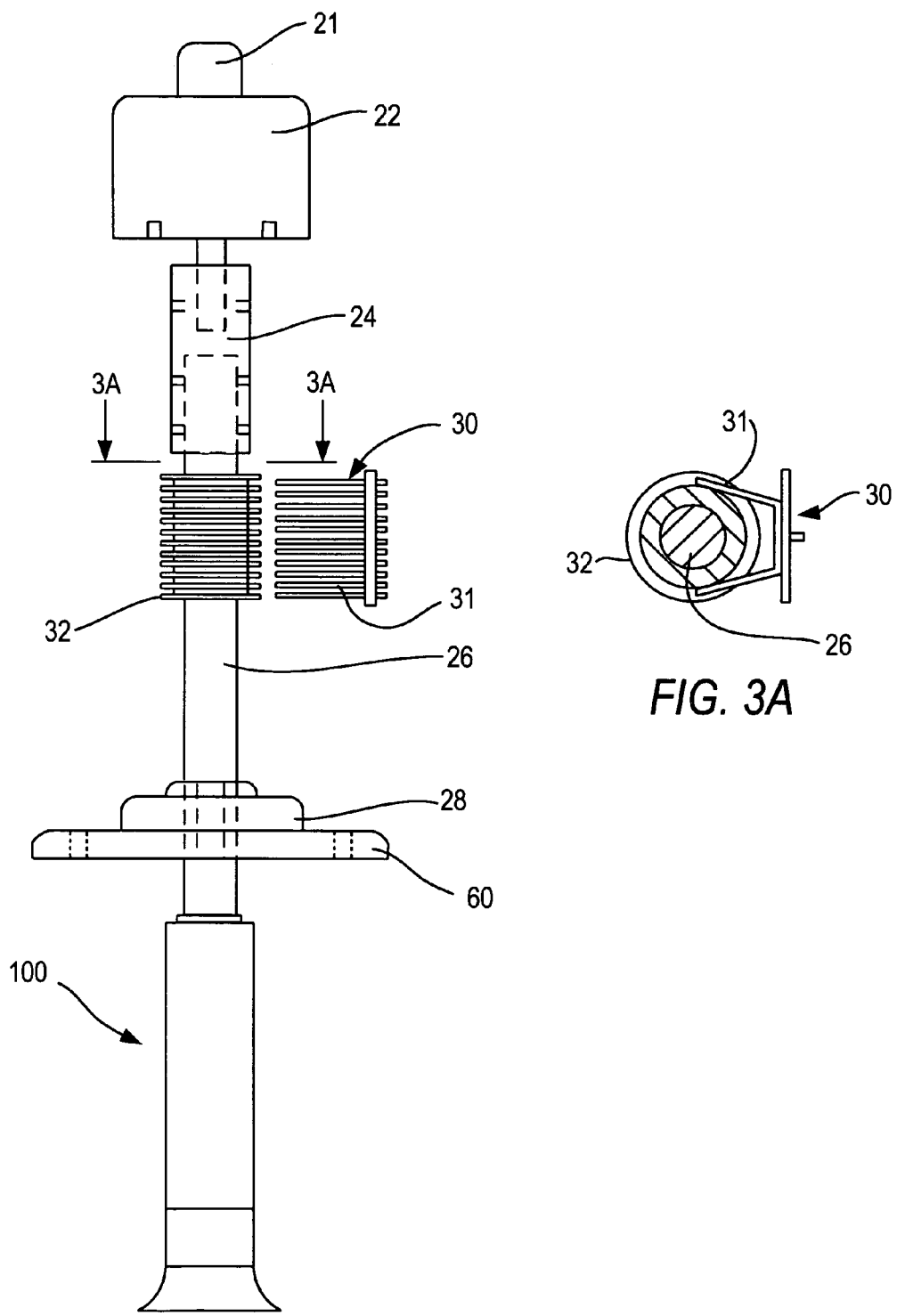
FIG. 3 is a schematic illustration of an elevational view of the rotating electrode test assembly with a cylindrical electrode in place and operably connected to a conventional test stand for providing electrical power and rotation to the assembly.

The use of the rotational test electrode assembly will be described in conduction with FIG. 3 in which a rotating disk is to be utilized. As shown in FIG. 3, the rotational assembly 20 comprises a variable speed motor 22 with speed indicator/controller 21. A mounting collar 24 couples the output shaft of motor 22 to drive shaft 26, which can be of any desired length to conveniently position the rotational assembly 20 for the manual attachment and removal of the respective rotational electrodes 100, and their placement in the polarization cell 40.

With continuing reference to FIG. 3, the drive shaft 26 passes through, and is supported for rotation by bearing member 28 that is mounted on supporting plate 36 which can be utilized to conveniently mount the apparatus on a bench, rack or other stable mounting device for convenient access.

A plurality of electrically conductive brushes 30 are mounted in slip-ring mounting member 32 on the drive shaft 26. As shown best in the cross-sectional view of FIG. 3A, the free-ends of the generally U-shaped brush elements 31 contact the rotating surface of the slip-rings.

The lower end of drive shaft 26 extending from the slip-ring assembly 32 is hollow to receive the plurality of electrical leads (not shown) that are connected to the plug 38 that is fitted to the end of the shaft 26. Plug 38 mates with socket 138 that is fitted to the end of rotating electrode shaft 140.

Figure 4:
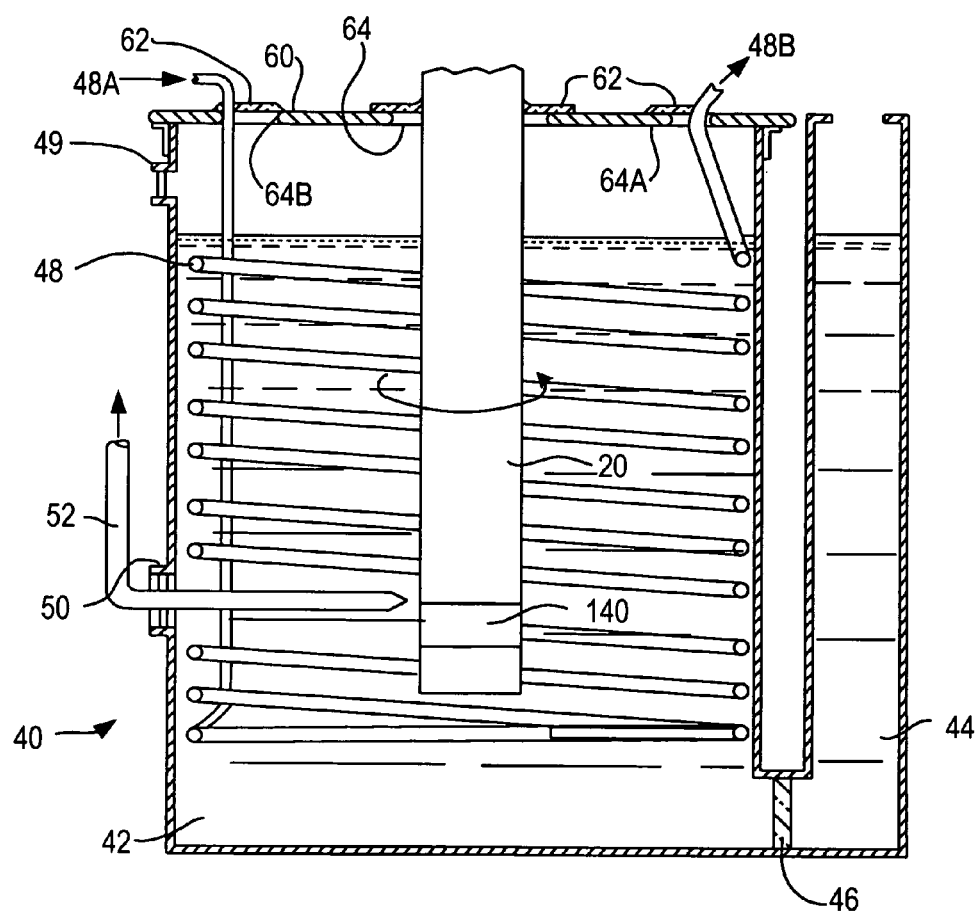
FIG. 4 is a schematic illustration of a side elevational view of the rotational test electrode assembly utilizing a disk electrode in operating position in a typical test cell.

Referring to the schematic illustration of FIG. 4, the corrosion testing apparatus 10 of the invention comprises a rotational electrode assembly 100, the lower portion of which has been fitted with a rotating cylindrical electrode (RCE) 150 in accordance with the description provided above, particularly with reference to FIG. 1.

The rotational assembly 100 is shown positioned in polarization cell 40. As shown FIG. 4, polarization cell 40 includes a first chamber 42 for receiving the rotating electrode and a second, smaller chamber 44 separated by a sintered glass member 46 located in a conduit joining the two chambers. The larger chamber 42 is provided with coil 48 through which can be passed a heat transfer fluid provided from an external source (not shown) in order to maintain a predetermined desired temperature differential between the heated electrode and the fluid.

A reference electrode 52 is introduced through a fluid-tight fitting 50 in a sidewall of chamber 42 or, alternatively, through a similar fitting (not shown) in removable cover 60. A counter electrode (not shown) is positioned in chamber 44.

Removable cover 60 is received in close-fitting relation over the open end of chamber 42 and is preferably provided with a plurality of openings for receiving in fluid-tight relation the shaft of the rotational assembly 20, as well as auxiliary devices that can include, e.g., a thermometer or other temperature sensing device; inlet and outlet tubes 48A and 48B, respectively, of cooling coil 48; gas inlet and removal conduits, e.g., to provide a nitrogen atmosphere for exclusion of oxygen, and to remove any gaseous by-products generated during operation of the apparatus; and to insert the reference electrode and/or other electrodes and probes that may be required for data collection and for alerting the conditions with the vessel 42.

Appropriately configured stoppers and/or seal members 62 are fitted into unused openings or around projecting tubes and the rotational assembly 100. A stopper 62 can be inserted to close the open end of smaller chamber 44.

EXAMPLE

A test cell in accordance with the invention consisting of two compartments was constructed with a first flanged working electrode compartment having a capacity of 2 liters and a 12 cm. diameter; the adjacent second counter electrode compartment being of the same height, had a 2.5 cm. diameter. The two compartments were connected with a tube of 25 mm diameter containing a full bore sintered class disk. The test cell was fabricated from a corrosion resistant, electrically insulative polymeric material.

A rubber stopper 50 was secured in a flanged opening in a side wall adjacent the bottom of the first cell. A capillary tube was passed through the stopper and connected to the reference electrode 52 with its tip that served as a Luggin probe being centrally positioned in the reaction vessel. The cell is carefully filled with a corrosive fluid sample that has been obtained from a heat exchanger feedline.

As in the embodiment illustrated in FIG. 4, a Luggin probe is shown positioned in close proximity to the RCE specimen. By way of background, the Luggin probe consists of a capillary tube which extends into the cell to a position proximate the electrode, the overvoltage of which is to measured. The capillary tube is connected by a salt bridge to a reference electrode, for example, to a calomel reference electrode, located outside the electrolytic cell. The Luggin probe is suitable for obtaining intermittent measurements, which is sufficient for laboratory testing and data collection purposes. When the RDE is utilized the Luggin probe is positioned below and proximate to the underside of the disk.

The polarization cell cover 60 is positioned below the lower portion of drive shaft 26, it being understood that the cover does not rotate and is large enough to receive the rotating shaft and an attached RDE or RCE when the polarization cell is brought into operating position below the support plate 36.

The test cell compartment 40 was covered with a 140 mm diameter flanged lid 60 having a 40 mm diameter central opening to receive the rotating assembly, electrode and driveshaft. Two other 20 mm adjacent openings are provided for use as may be needed for specific tests. The inlet and outlet tubes for the cooling coil were passed through the side wall of the first compartment (not shown).

The rotating electrode supporting shaft 100 is fitted with an internally mounted electric resistance heating device. A protective insulating cover fabricated from PTFE 140 is employed to isolate the conductive member from the effects of the corrosive fluid in which the rotating electrode is to be immersed.

The rotating electrode assembly 100 is joined to the electrical plug 38 through socket 138. The electrode coupling collar 54 that is mounted on the lower end of drive shaft 26 is secured by thumbscrews 55 to the upper end of shaft 140.

The rotating electrode assembly 100 is passed through central opening 64 in cover 60 and sliding seal 62 is put in place. The power to the heating device 130 is turned on and thermocouple readings are observed to determine that the RCE has reached the desired temperature. Thereafter, the power to the drive motor 22 is adjusted by controller 21 to obtain the desired revolutions for the testing of the RCE.

After the test has been concluded, the seal 62 is removed and the electrode assembly 100 is withdrawn from the test cell. The thumbscrews 55 on the electrode coupling 54 are released and the socket 138 is separated from the electrical plug 38. The assembly 100 is then washed and cleaned to remove any residues of corrosive fluid and disassembled to recover the electrode 150 for further testing and analysis.

As will be understood from the above description, the apparatus of the invention provides the following benefits and advantages for both the RDE and RCE devices in a variety of modes of operation:

1. a uniform heat flux emanates from the surface of the cylindrical or disk specimen to the surrounding fluid during operation in the polarization cell;
2. a uniform temperature is provided over the entire surface of the specimen;
3. a uniform boundary layer thickness is presented over the entire specimen surface;
4. the edge of the rotating disk or cylinder shaft has no effect on the uniformity of the boundary layer conditions;
5. no electric current flows from the drive motor to the working electrode; and
6. cylindrical specimens having different heights and associated surface areas can be used interchangeably in a single rotating electrode mounting member.

The apparatus of the invention is prepared for operation and recording of data by filling the test cell with the test fluid, e.g., a corrosive liquid of known composition at a predetermined temperature. The heat transfer fluid is circulated through coils 48 at the same predetermined temperature. The control electrode is inserted into chamber 44 and the rotational electrode fitted with a cylindrical electrode specimen as shown in FIG. 3 is passed through the central opening 64 in cover 60 for immersion in the corrosive test liquid. The Luggin probe is fitted through seal 50 and positioned proximate the cylindrical specimen 110. Seal 62 is positioned around the rotating shaft assembly 102. As will be understood from the above description, a single rotational shaft is provided on which can be installed either a disk electrode or cylindrical electrode specimen. The apparatus is capable of evaluating the electrochemical behavior of metals and the performance of corrosion inhibitors under static conditions, hydrodynamic conditions of laminar flow and turbulent flow, isothermal and heat transfer conditions, and combinations thereof.

The apparatus permits the interfacial heat transfer coefficient and interfacial temperature for the cylindrical electrode specimen to be estimated by conventional mathematical modeling and the utilization of analogies among the transport phenomenon for momentum, heat and mass transfer. The apparatus permits data to be collected that is required for conducting quantitative corrosion aid corrosion preventive research for industrial application with a minimum of data manipulation.

It will also be understood from the above description that the apparatus and method of the invention is particularly useful for evaluating corrosion conditions and the effect of inhibitors as applied specifically to industrial cooling systems, e.g., heat exchangers. The apparatus and method of the invention also provides a reliable, reproducible and inexpensive means for evaluating the inhibitive characteristics and compatibility of any of the numerous chemical compounds utilized industrially under conditions that simulate closely those of flow, mass and heat transfer in specific industrial applications.

As will be apparent from the above description to one of ordinary skill in the art, further modifications can be made to the assembly without departing from essential features of the invention as defined in the following claims.

I claim:

1. A rotational test electrode assembly for use in a corrosive fluid environment comprising:
    a) a generally cylindrical heat and electrically conductive member having an annular portion, a solid portion, and mounting means for attaching a rotational electrode in close-fitting heat and electrically conductive relation, the electrode being selected from the group consisting of cylindrical and disk electrodes;
    b) a heating device positioned inside of the annular portion and in heat exchanging relation with the solid portion of the conductive member;
    c) a corrosion resistant external protective member that surrounds a portion of the heat conductive member in close-fitting relationship;
    d) electrical terminal means for receiving a plurality of external electrical connectors that is mounted on the protective member opposite the portion of the conductive member on which the rotational electrode is mounted; and
    e) driving means to rotate the rotational test electrode assembly.

2. The rotational test electrode assembly of claim 1, wherein the mounting means are mating threaded surfaces.

3. The rotational test electrode assembly of claim 1 which further comprises a plurality of thermocouples in contact with the conductive member, each of the plurality of thermocouples having an electrical lead in contact with the terminal means.

4. The rotational test electrode assembly of claim 1, wherein the protective member comprises at least two portions, and at least one of the portions engages a surface of the rotational electrode in fluid-tight relation when assembled for operation.

5. The rotational test electrode assembly of claim 1 which further comprises mounting means proximate the electrical terminal means for coupling the assembly to the rotational drive means.

6. The rotational test electrode assembly of claim 1, wherein the heating device is an electrical resistance heater.

7. The rotational test electrode assembly of claim 1, wherein the conductive member is brass.

8. The assembly of claim 1 which further comprises an electrical lead extending from the interior surface of the annular portion of the conductive member to the electrical terminal.

9. The rotational test electrode assembly of claim 1, wherein the protective member is formed from an electrically insulative polymer.

10. The rotational test electrode assembly of claim 9, wherein the polymer is selected from the group consisting of polytetrafluoroethylene, polyethylene, polypropylene, polyvinyl chloride, and copolymers thereof.

11. The rotational test electrode assembly of claim 1, wherein the mounting means for attaching the rotating disk electrode is a threaded aperture located in the end of the solid portion of the conductive member positioned to receive a cooperatively threaded shaft extending from the disk electrode, whereby the surfaces surrounding the aperture and the shaft are in close-fitting relation when assembled.

12. The assembly of claim 11, wherein the disk electrode includes a peripheral shoulder that engages a surface of the protective member in fluid-tight relation when assembled.

13. The rotational test electrode assembly of claim 1, wherein the mounting means for attaching the cylindrical electrode comprises a threaded surface formed on the conductive member and extending inwardly from the end defining the solid portion of the conductive member and a cooperatively threaded interior surface of the cylindrical electrode, whereby said cylindrical electrode is assembled on the conductive member to a position proximate the heating device.

14. The assembly of claim 13, wherein the protective member consists of a first cylindrical portion terminating in fluid-tight relation with one end of the cylindrical electrode and second portion that terminates in fluid-tight relation with the other end of the cylindrical electrode.

15. The assembly of claim 14, wherein the second portion is in the form of a cylindrical cup having an internally threaded sidewall that is cooperatively received on the threaded surface of the conductive member.

16. The rotational test electrode assembly of claim 1, wherein the mounting means comprises a reinforcing cylindrical flanged sleeve that is received in close-fitting relation on the interior of the protective member and the flange extends over the end of the protective member.

17. The assembly of claim 16, wherein the flanged sleeve is metal.

18. The assembly of claim 16, wherein the end of the sleeve positioned inside the protective member is displaced from the end of the annular portion of the conductive member by an electrically insulative air gap, whereby the electrode is electrically isolated from stray electrical currents during operation.

* * * * *

UNITED STATES PATENT AND TRADEMARK OFFICE
CERTIFICATE OF CORRECTION

PATENT NO.        : 7,320,245 B2                                  Page 1 of 1
APPLICATION NO.   : 10/533490
DATED             : January 22, 2008
INVENTOR(S)       : Jaralla et al.

It is certified that error appears in the above-identified patent and that said Letters Patent is hereby corrected as shown below:

On the title page,

[*] Notice:    Subject to any disclaimer, the term of this patent is extended or adjusted under 35 USC 154(b) by 145 days Delete the phrase "by 145 days" and insert -- by 144 days --

Signed and Sealed this

Twenty-eighth Day of October, 2008

JON W. DUDAS
*Director of the United States Patent and Trademark Office*